United States Patent [19]

Kathawala

[11] 4,456,619
[45] Jun. 26, 1984

[54] AMIDES OF 2-ALKYNOIC ACIDS AND USE FOR INHIBITING ACCUMULATION OF CHOLESTEROL ESTER IN ARTERIAL WALLS

[75] Inventor: Faizulla G. Kathawala, Mountain Lakes, N.J.

[73] Assignee: Sandoz, Inc., E. Hanover, N.J.

[21] Appl. No.: 76,460

[22] Filed: Sep. 17, 1979

Related U.S. Application Data

[63] Continuation-in-part of Ser. No. 943,340, Sep. 18, 1978, abandoned.

[51] Int. Cl.$^3$ .............. C07C 103/133; C07C 103/737; A61K 31/16
[52] U.S. Cl. .................................. 424/324; 424/320; 260/404; 260/413
[58] Field of Search ................ 260/558 B, 558 P, 404; 424/324

[56] References Cited

U.S. PATENT DOCUMENTS

| | | | |
|---|---|---|---|
| 3,995,059 | 11/1976 | Fukumaru et al. | 424/320 |
| 4,021,224 | 3/1977 | Pallos et al. | 260/561 M |
| 4,139,563 | 2/1979 | Metcalf et al. | 260/561 M |

FOREIGN PATENT DOCUMENTS

40-9134  5/1965  Japan.
40-10571  5/1965  Japan.

OTHER PUBLICATIONS

Noller, 3rd Ed., "Chem. of Organic Compounds", pp. 207, 208 & 868, W. B. Saunders Co., Phila. Pa., 1965.
Suyamya et al., Chem.–Abst., 66, 29058y.

Primary Examiner—Paul M. Coughlan, Jr.
Assistant Examiner—D. B. Springer
Attorney, Agent, or Firm—Gerald D. Sharkin; Richard E. Vila; Frederick H. Weinfeldt

[57] ABSTRACT

The compounds are secondary amides of the formula

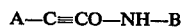

$$A-C\equiv CO-NH-B$$

wherein
A is alkyl, a mono- or poly-ethylenically unsaturated acyclic hydrocarbon chain, or a hydrocarbon chain having from 1 to 4 cyclopropanyl units thereon; and
B is a radical which may be of the phenyl, benzyl, phenylalkyl, benzocycloalkyl or indol- type, e.g., N-[1-phenyl-2-(p-methylphenyl)-ethyl]-oct-2-ynoylamide.

The compounds are useful as pharmaceutical agents.

31 Claims, No Drawings

AMIDES OF 2-ALKYNOIC ACIDS AND USE FOR INHIBITING ACCUMULATION OF CHOLESTEROL ESTER IN ARTERIAL WALLS

This application is a continuation-in-part of copending application Ser. No. 943,340 filed Sept. 18, 1978, abandoned.

This invention relates to organic compounds and more particularly to secondary amides of 2-alkynoic acids, as well as to their use as pharmaceutical agents, and to pharmaceutical compositions containing such compounds.

The compounds of this invention may be conveniently represented by compounds of formula I:

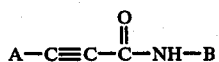

wherein A is of type a) an alkyl radical having from 1 to 23 carbon atoms;

type b) an alkenyl or alk-(poly)en-yl radical having from 7 to 23 carbon atoms and from 1 to 4 ethylenically unsaturated positions; or type c) an ethylenically unsaturated hydrocarbon chain being from 7 to 23 carbon atoms in which each unsaturated ethylene moiety, ie. of the formula:

is replaced by a cyclopropanyl group of the formula

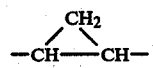

said A having 1 to 4 such cyclopropanyl groups (and said A hence being a saturated chain): and B is of:
type a) an aralkyl radical of the structure

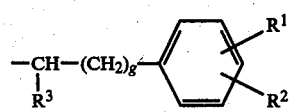

wherein g is 0 or 1;

$R^1$ is a hydrogen atom, halo having an atomic weight of from about 19 to 80, ie. fluoro, chloro or bromo, alkoxy having from 1 to 3 carbon atoms, eg methoxy; or alkyl having from 1 to 3 carbon atoms, eg methyl;

$R^2$ is a hydrogen atom, alkyl having from 1 to 3 carbon atoms, alkoxy having from 1 to 3 carbon atoms, or halo having an atomic weight of from about 19 to 36, ie fluoro or chloro; and $R^3$ is subtype i) a hydrogen atom, subtype ii, a phenyl radical of the structure

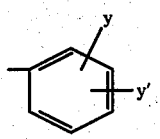

wherein y is a hydrogen atom, halo having an atomic weight of from about 19 to 80, ie. fluoro, chloro or bromo, alkoxy having from 1 to 3 carbon atoms, eg methoxy; or alkyl having from 1 to 3 carbon atoms, eg methyl; and y' is a hydrogen atom, alkoxy having from 1 to 3 carbon atoms, alkyl having from 1 to 3 carbon atoms, or halo having an atomic weight of from about 19 to 36, ie fluoro or chloro; or subtype iii, a benzyl radical of the formula

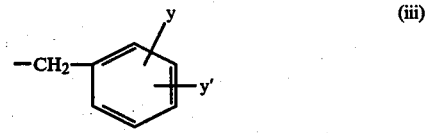

wherein y and y' are as defined above; or subtype iv) alkyl having from 1 to 8 carbon atoms;
type b) a phenyl radical of the structure of:

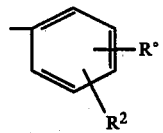

wherein $R^2$ is as defined above, and $R°$ is a hydrogen atom, halo having an atomic weight of from about 19 to 80, ie fluoro, chloro or bromo, alkyl having from 1 to 3 carbon atoms; alkoxy having from 1 to 3 carbon atoms; or a radical of the structure $R^f$:

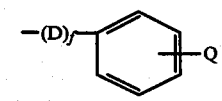

in which
D is —CH$_2$— or —O—;
f is 0 or 1; and
Q is a hydrogen atom, halo having an atomic weight of from about 19 to 80, alkoxy having from 1 to 3 carbon atoms, or alkyl having from 1 to 3 carbon atoms;
type c) an indolyl radical of the structure:

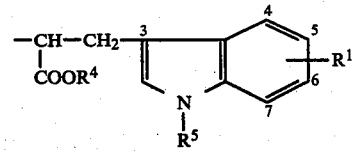

wherein
$R^1$ is as defined above;
$R^4$ is alkyl having from 1 to 8 carbon atoms or benzyl (unsubstituted); and
$R^5$ is a hydrogen atom, alkyl having from 1 to 8 carbon atoms or benzyl (unsubstituted); or
type d) a benzocycloalkyl nucleus of the structure:

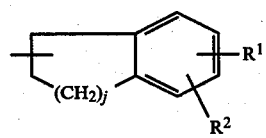

wherein $R^1$ and $R^2$ are as defined above; and j is a whole integer of from 1 to 4.

Compounds I may be obtained by acylation (process a) of a primary amine of the formula II:

$$H_2N-B \qquad (II)$$

in which B is as defined above (or an acid addition salt thereof) with a carboxylic acid, or derivative thereof, bearing the moiety $A-C\equiv C-$, (A being as defined above). Such acylation may be carried out by conventional means employed in converting a primary amine function to its corresponding secondary amide, such as are reported in the literature.

A convenient method of preparing a compound I comprises reacting a compound II (in free or acid addition salt form thereof, eg. the hydrochloride) with a pyrrolidine-2,5 dione of the formula III:

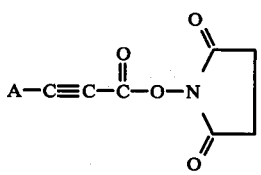

in which A and B are as defined above, under anhydrous conditions, in the presence of an inert organic solvent, eg a hydrocarbon, such as toluene, a halogenated hydrocarbon such as methylene chloride or dichloroethane, or an ether such as a dimethyl ether of a glycol, such as ethylene glycol, at moderate temperatures, for example from about $-20°$ to $+120°$ C., preferably from abut $0°$ to $30°$, or at the reflux temperature of the reaction mixture. Time and temperature are not critical for the reaction; from about two to four hours is usually satisfactory. Where II is used in the form of an acid addition salt, an acidic acceptor is also employed, e.g., a tertiary amine, such as triethylamine.

The above-described compounds III are obtainable by reaction (process b) of 2-alkynoic acid of the formula IV

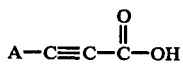

in which A is as defined above with 1-hydroxy-pyrrolidine 2,5-dione (V)

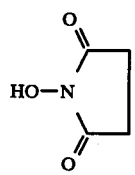

under anhydrous conditions, in the presence of an inert organic solvent, eg a halogenated hydrocarbon, such as dichloroethane, or an ether eg a dimethylether of a glycol, such as ethylene glycol, and in the presence of a dehydrating agent, such as dicyclohexylcarbodiimide (DCC), at moderate temperatures eg from about $-10°$ to $+100°$ C., preferably at about $-10°$ to $+30°$. 1-Hydroxy-pyrrolidine-2,5-dione is also known as 1-hydroxy-succinimide.

If desired, a compound III may be prepared by process b) and then used directly for process a), without recovery.

The anhydrous conditions employed in processes a) and b) are maintained in the manner customarily practiced, eg by use of dry solvents, flushing apparatus with dry $N_2$, etc.

Some compounds IV are known and may be obtained as described in the literature, while those not known may be obtained by adaptation of methods described for the preparation of their known analogs.

If desired, Compounds IV may be conveniently obtained by a series of process steps involving first, reaction (process C1) of a Wittig reagent of the formula VI:

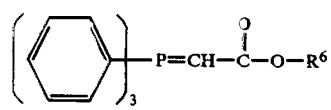

in which $R^6$ is alkyl of from 1 to 6 carbon atoms, preferably ethyl, with an acyl chloride of the formula VII:

in which A is as defined above, to obtain a phosphoran intermediate of the formula VIII:

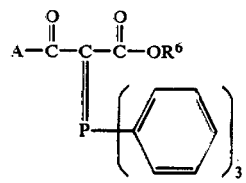

in which A and $R^6$ are as defined above. Compounds VIII are then pyrolyzed (process C2) to form alkynoic acid esters of the formula IX:

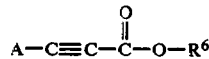

in which A and $R^6$ are as defined above. Saponification (process C3) of compounds IX yields the corresponding acids (Compounds IV) desired for process b). These process steps are discussed individually in further detail below.

Process C1) is suitably carried out under anhydrous conditions in an inert organic solvent, e.g., a hydrocarbon such as benzene or toluene, or an ether, such as diethyl ether, tetrahydrofuran, or a dimethyl ether of a glycol, at moderate temperatures, e.g., about $-5°$ to $200°$ C., preferably at room temperature, i.e. about $20°$ to $30°$ C. or at the reflux temperature of the solvent. The preferred ratio of equivalents of VI to VII is about 2:1.

In process C2), the phosphoran intermediates (VIII) are converted to their corresponding Compounds IX by heating, i.e., at about $50°$ to $300°$ C., under vacuum. A convenient method of carrying out Process C2) at higher temperatures, e.g. at over about $180°$ C., is by short path distillation-pyrolysis (under vacuum, e.g., 0.05 to 0.5 mmHg). An apparatus which is particularly useful for such a procedure is known as a "kugelrohr".

The saponification step, Process C3), may be carried out as is conventional in the art. For example, a Compound IX may be treated with an aqueous inorganic base, such as a 2 to 10% solution of an alkali metal hydroxide, e.g., sodium hydroxide or potassium hydroxide, at temperatures of, for example, from about 15° to 120° C., preferably also in the presence of a water-miscible solvent such as a lower alkanol, e.g., having from 1 to 3 carbon atoms, such as methanol or ethanol. A convenient temperature from the saponification is room temperature, ie about 20° to 30° C.

Compounds VII employed in process C1, described above, are either known and obtainable by methods described in the art, or where not known, may be obtainable by adapting methods analogous to those reported in the art for the preparation of their known analogs. Many Compounds VII are commercially available. For example, compounds VII may be prepared by treating an A-bearing carboxylic acid of formula X:

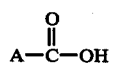       X with a chlorinating agent (process d). In those instances where A is of type b), particular care should be exercised in carrying out process d) in selecting the chlorinating agent and reaction conditions to insure that alteration of the A portion of a compound X is avoided or at least minimized, ie that the ethylenically unsaturated positions present on the A radical do not become chlorinated. For example, a compound X in which A is of type b) may be converted to its corresponding acyl chloride (VII) by treatment with oxylyl chloride at moderate temperatures, eg 20° to 30° C., in an inert organic solvent, eg diethyl ether.

It will be noted that A may be any of three types, ie a) alkyl, ie saturated acyclic hydrocarbon; b) alkenyl or alk-(poly)enyl, ie mono or poly-ethylenically unsaturated; or c) a saturated hydrocarbon chain bearing from one to four cyclopropanyl units. Particular embodiments of Compounds I with particular respect to A as of types b) and c) are further described below. In the discussion, when A is of type b) it is designated as A'; and when A is of type c) it is designated as A''.

With respect to compounds I where A is of type b), ie A=A', embodiments of this invention are Compounds I in which A' is of the formula:

A1)    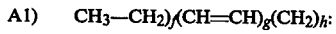

or

A2)    

wherein when A' is A1) then f=1 to 10, g=1 to 4, and h=3 to 9;

particularly where f=5 or 7, q=1, and h=7; and when A' is A2) then n=1 to 4, m=2 to 4, and p=1 to 7;

particularly where n=1 or 4, m=from 2 to 4 and p=2 or 6.

The total number of carbon atoms in A1 or A2 conforms to the definition of A', above. Thus, where A' is the residue of an acid (X) or acyl chloride (VII), having from 8 to 24 carbons; A' will have from 7 to 23 carbons and from 1 to 4 unsaturated positions. A' is preferably unbranched. Also generally preferred as sources of A', are the fatty acid derivatives of the natural fatty acid order, ie those in which A' represents an odd number of carbon atoms of from 7 to 23 and accordingly the A'—C=O moiety has an even number of carbon atoms of from 8 to 24.

Examples of acids suitable to provide A' are given in tables I and II below:

TABLE I

| carbons in A'—C=O | A' = A1 | | | acid |
|---|---|---|---|---|
| | f | g | h | |
| 16 | 5 | 1 | 7 | palmitoleic |
| 18 | 7 | 1 | 7 | oleic |
| 18 | 10 | 1 | 4 | petroselenic |
| 18 | 5 | 1 | 9 | vaccenic |
| 18 | 3 | 3 | 7 | punicic (or eleostearic) |
| 18 | 1 | 4 | 7 | parinaric |
| 20 | 9 | 1 | 7 | gadoleic |
| 22 | 9 | 1 | 9 | cetoleic |

TABLE II

| carbons in A'—C=O | A' = A2 | | | acid |
|---|---|---|---|---|
| | n | m | p | |
| 18 | 4 | 2 | 6 | linoleic |
| 18 | 1 | 3 | 6 | linolenic |
| 20 | 4 | 4 | 2 | arachidonic |

Those compounds I wherein A' is derived from oleic, linoleic, linolenic, arachidonic or palmiloleic acids are particularly preferred.

It will be appreciated that the unsaturated acids which provide the moiety A' occur in isomeric forms due to the presence of the one or more unsaturated positions. The particular isomeric form of the A' moiety in a parent acid will remain the same in the resulting Compound I, since the structural configuration of the A' moiety is not changed by the processes yielding compounds I. Compounds I wherein the hydrogen atoms qn the pair of carbons of each unsaturated position of the A'-moiety are in the cis configuration are preferred.

When A is of type A'', then cyclopropanyl group-bearing fatty acids suitable as compounds X, may be conveniently obtained by converting the unsaturated positions of corresponding long chain ethylenically unsaturated fatty acids to cyclopropanyl groups. It will be appreciated that each olefinic unit: —CH=CH— is thus replaced by a cyclopropanyl unit

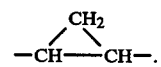

Since each cyclopropanyl unit contributes an additional carbon atom beyond the number in the linear hydrocarbon "backbone" of a radical A″, the total number of carbon atoms in A″ will equal the number of carbon atoms in the non-cyclic portion plus the total number of methylene carbon atoms of the cyclopropanyl units thereon.

For example, compounds suitable as cyclopropanyl-bearing acids (X) in which A=A″, are obtainable by treatment of a corresponding mono- or poly-unsaturated long chain fatty acid with methyleneiodide ($CH_2I_2$) by the Simmons-Smith method (described in J.A.C.S. 81, 4256 (1959)).

For preparing compounds X bearing a single cyclopropanyl unit, the starting acids may possess either the cis-oid or trans-oid configuration. When acids with cis-oid configuration are used, the Simmons-Smith reaction, used for preparing the corresponding "cyclopropane" acids (X), leads only to cis "cyclopropane" acids, and similarly the trans-acids gives the corresponding trans-"cyclopropane" acids. Mixtures will of course lead to corresponding mixture. If desired, the starting cyclopropane acid may be resolved into its antipodes, and a particular antipode product (III) then reacted with the desired optical isomer of a compound II, to give the corresponding isomeric product (I) in relatively pure isomeric form.

Similarly, for preparing cyclopropane acids (X) bearing two or more cyclopropanyl units, the starting olefinic acids have a corresponding number of double bonds, and the Simmons-Smith reaction leads to a mixture of diastereomeric acids, which may be separated before further reacting.

Since compounds I having only one cyclopropanyl unit have a lesser number of asymmetric carbon atoms than those derived from acid of greater unsaturation, they are generally easier to refine and are therefore, preferred from that standpoint, where case of purification is an important factor in their preparation.

In general it is preferred that A″ is unbranched. It is further preferred that each pair of hydrogen atoms bound to the tertiary carbon atoms of each cyclopropanyl group is in the cis configuration.

A preferred class of Compounds I in which A is of type c, ie A=A″, are those wherein A″ is a cyclopropanyl-bearing hydrocarbon radical of the formula A3:

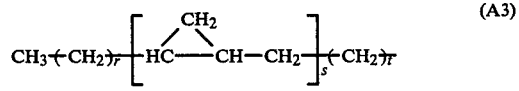
(A3)

wherein r is a whole integer of from 1 to 15; s is 1 or 2; and t is a whole integer of from 1 to 13, provided that when s is 1, then r+t is from 3 to 19, and when s is 2 then r+t is from 2 to 16; and particularly those having in addition to the various preferences discussed above, one or more of the following characteristics with respect to the A″-moiety: (1) r+t=7 to 19 when s is 1; or r+t=4 to 16 when s=2; (2) r+t=an odd number when s=1, and even number when s=2; and (3) when s=1, then r=5 or 7 and t=6; and when s=2, then r=4 and t=6.

In view of the above-presented preferences it will be appreciated that it is particularly preferred that in compounds I the A″-moiety is derived from mono- or di-unsaturated fatty acids (or esters thereof) of the type found in nature, especially palmitoleic oleic acid (s=1); and linoleic acid (s=2).

With respect to B, when it is of type a) or b) and R° is not $R^1$, it is preferred that when $R^1$, R° or y is other than a hydrogen atom and $R^2$ (or y′) is a hydrogen atom, that R°, or $R^1$, or y be located at the 2- or 4-position; and that when $R^2$ (or y′) is also other than a hydrogen atom that $R^1$ or R° and $R^2$ (or y and y′) are the same, and it is additionally preferred that they be located at the 2- and 4- or 6-positions of the phenyl ring. When B is of type a) where g=1, and $R^3$ is of type ii), then B- ca be a 2-(phenyl)-phenethyl radical, e.g. 1-phenyl-2-(p-methylphenyl)-ethyl radical; or $R^3$ is of type iii), then B can be an α-(benzyl)-phenylethyl radical.

With particular respect to the substituent R° when it is a radical $R^f$, it will be appreciated that when D=$CH_2$ and f=1, then the radical $R^f$ is of the benzyl type. When D=oxygen and f=1, then the radical $R^f$ is of the phenoxy-type. When f=zero, then the radical $R^f$ is of the phenyl-type. Hence, when B is of type b) and R° is of type $R^f$ where f=zero, then B can be a biphenylyl radical. The radical $R^f$ is preferably at the para-position. When Q is other than a hydrogen atom, it is preferably at the para-position.

With respect to B, when it is of type c), it is preferred that when $R^1$ is other than a hydrogen atom, it be located at the 5-position of the indole nucleus. It is also preferred that when $R^4$ is alkyl, it is unbranched, particularly ethyl.

With respect to B when it is of type d) it is preferred that when $R^1$ is other than a hydrogen atom, that it be located at a carbon atom ortho to the ring junction; and that when $R^2$ is also other than a hydrogen, it is preferred that it be the same as $R^1$, and it is additionally preferred that it be in para-relationship to $R^1$. It is additionally preferred that the amide group be linked to a carbon of the cycloalkyl moiety which is directly bonded to a ring junction carbon. It is also preferred that j be 1, ie, that the benzocycloalkyl nucleus be indanyl, and particularly 1-indanyl.

In the above-presented definitions, when R°, $R^1$ or y is halo, it is preferably fluoro or chloro, and particularly chloro; and when $R^2$ or y′ is halo it is preferably chloro.

Particular embodiments of this invention are the compound N-[1-phenyl-2-(p-methylphenyl)-ethyl]-oct-2-ynoylamide of Example 2, and pharmaceutical compositions containing said compound, as well as the use of said compound and compositions containing said compound as described herein.

In addition to those specifically discussed above, reagents and reactants described herein, e.g., compounds II, IV, V, VI, VII, VIII, IX and X, are known and obtainable by known means, or where not known, may be obtained by adaptation of methods reported in the literature for the preparation of known analogs; many such compounds being commercially available.

The preparation of the final compounds of this invention I by the above-described processes may be conveniently represented by Reaction Scheme A, below, in which A, B, and $R^6$ are as defined above.

REACTION SCHEME A

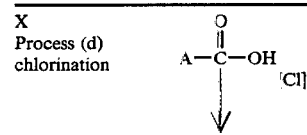

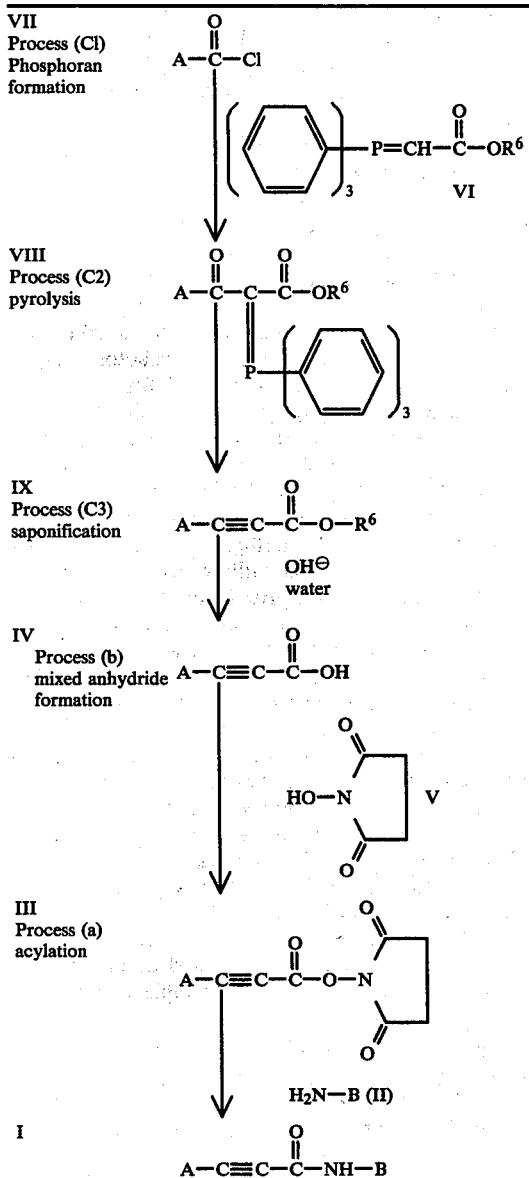

STATEMENT OF UTILITY

The compounds of formula I of this invention are useful as pharmaceutical agents in animals. In particular, the compounds of the formula I are useful in controlling the cholesterol ester content of mammalian arterial walls and are therefore particularly indicated for use as antiatherosclerotic agents, ie. agents useful in the prophylactic treatment of atherosclerosis and in the controlling of atherosclerotic conditions due to cholesterol ester accumulation in the arterial walls. Such ability of the compounds of the formula I is indicated by known test procedures in which the total cholesterol ester content of cultured cells is shown to be reduced by a test compound, as compared to untreated cells, and carried out, for example, by the following procedures:

(A) Cell culture

Rhesus monkey smooth muscle cells (from the arterial, eg. aorta wall) obtained by the method of K. Fisher-Dzega et al (Experimental and Molecular Pathology 18, 162–176 (1973)) are routinely grown in 75 $cm^2$ tissue culture flasks using Minimum Essential Medium (Eagle) supplemented with 10% fetal bovine serum. For testing a 75 $cm^2$ flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 1 mg per 100 ml of media of the test compound are added. The dishes are returned to the incubator for an additional 24 hours. All operations through to the final incubation are preformed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical graduated centrifuge tube. The cells are washed three times by suspending in an isotonic salt solution, centrifuging at 800×g for 10 minutes and aspirating the supernatant fluid.

(B) Cell extraction procedure

An appropriate volume of isopropyl alcohol (about 1 ml/mg protein) is then added to the cell pellet and the sample sonicated with a micro probe (140×3 mm) for 10 seconds with a "LO" setting of 50 on a Bronwell Biosonik IV. After centrifugation for 15 minutes at 800×g, the clear supernatant is decanted and an aliquot taken for cholesterol analysis.

The residue is dissolved in 0.1N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml of free reagent (Reagent A, Table 1 below) is added to a 10×75 mm disposable glass test tube to which 20 μl of the isopropyl alcoholic solution is added and mixed. After standing at room temperature for approximately 5 minutes, 0.8 ml of 0.5N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead of the free reagent and the samples are incubated for 20 minutes at 37° C. before the addition of the 0.5N sodium hydroxide solution (Reagent C, Table 1).

Alternatively, the assay for cholesterol, ie Step C (above) obtained from Steps A and B, may be carried out by the method of Ishikawa et al (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

TABLE 1

Composition of Reagents for Cholesterol Determination

| | | |
|---|---|---|
| A. Free Cholesterol Reagent | | |
| Sodium phosphate buffer pH 7.0 | .05 | M |
| Cholesterol oxidase | .08 | U/ml |
| Horseradish peroxidase | 30. | U/ml |
| p-Hydroxyphenylacetic acid | .15 | mg/ml |
| B. Total Cholesterol Reagent | | |
| Sodium phosphate buffer pH 7.0 | .05 | M |
| Cholesterol ester hydrolase | .08 | U/ml |
| Cholesterol oxidase | .08 | U/ml |
| Horseradish peroxidase | 30. | U/ml |
| Sodium taurocholate | 5. | mM |
| Carbowax-6000 | .17 | mM |
| p-Hydroxyphenylacetic acid | .15 | mg/ml |
| C. Sodium Hydroxide Solution | .5N | |

Following the above-described test method, comparative test results were carried out and are reported in Table 2 below, in which monkey aortic smooth muscle cells were originally obtained from Dr. K. Fisher-Dzoga: Univ. of Chicago, the test compound (Compound A) is N-[1-phenyl-2-(p-methylphenyl)-ethyl]-oct-2-ynoylamide (of Example 2).

TABLE 2

| | Protein | Comparative Test Cholesterol (μg/mg cell protein) | | | | |
|---|---|---|---|---|---|---|
| Com- | mg/ | | | Ester | | % from |
| pound | culture | Total | Free | Amount | mean** | control |
| Con- | 0.378 | 83.41 | 38.78 | 44.63 | 42.0 ± 1.4 | |
| trol | 0.442 | 75.41 | 35.43 | 39.98 | | |
| | 0.376 | 79.07 | 37.66 | 41.41 | | |
| A | 0.414 | 60.94 | 47.49 | 13.45 | 16.5 ± 1.6* | 61 ↓ |
| A | 0.362 | 67.21 | 49.48 | 17.73 | | |
| A | 0.302 | 68.64 | 50.20 | 18.44 | | |

REF: 644/44
*Significant at p = .01
**± Standard Error

As is the present understanding in the art, controlling the total cholesterol content of an arterial wall by inhibiting the accumulation thereof by reducing the cholesterol ester content thereof, advantageously inhibits the formation of plaques in the arterial wall.

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of formula I are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams preferably from about 100 milligrams to 2,000 milligrams. Dosage forms suitable for internal use comprise from about 25 to 2,500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The preferred pharmaceutical compositions from the stand-point of ease of preparation and administration are solid compositions, particularly tablets and hard-filled or liquid-filled capsules.

Representative formulations for administration orally three times a day prior to feeding in the treatment of atherosclerosis are gelatin capsules prepared by conventional techniques to contain the following

| Ingredient | Weight | (in Mg.) |
|---|---|---|
| N—[1-phenyl-2-(p-methyl-phenyl)-ethyl]-oct-2-ynoylamide. | 300 | 300 |
| Corn oil | 500 | |
| lactose | | 200 |

Examples of the preparation of intermediates and final products are presented hereafter for purposes of illustration. In the examples all temperatures are centigrade, and room temperature is 20° to 30° C., unless indicated otherwise.

Preparations

The following examples illustrate methods of preparing starting materials (Compounds III) useful in preparing the final compounds of the invention ie Compounds I.

Preparation 1

Preparation of 1-(1-oxo-eicosa-11,14-dien-2-ynyloxy)-Pyrrolidine-2,5-dione (cis,cis isomer)

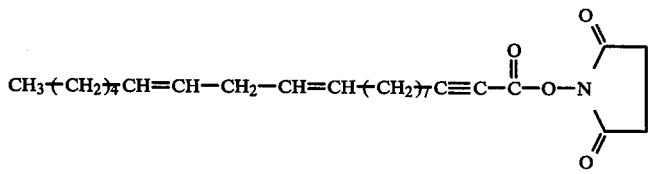

Step a ethyl 2-(triphenyl phosphoranylidene)-3-oxo-eicosa-11,14-dien-oate (cis,cis isomer); (by process C1)

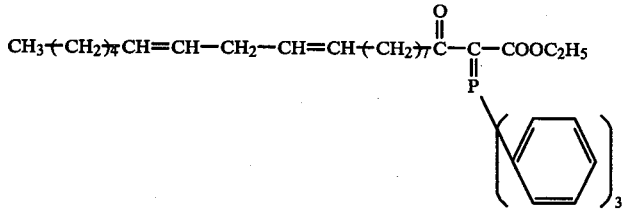

47 g (130 mmole) of carbethoxyethylidene-triphenyl-phosphorane are dissolved in 150 ml of warm toluene, the resulting solution cooled to room temperature, and 20 g (66.9 mmole) of linoleoyl chloride in 100 ml of toluene added, dropwise, with vigorous stirring. The reaction mixture is then stirred for about 16 hours at room temperature. The reaction mixture is then filtered, and the filtrate concentrated under low vacuum) to obtain the crude title product of this step as a viscous yellow oil, which is then refined by dissolving in methylene chloride and filtering through a silica gel column, then concentrated for use in the next step.

Step b) ethyl eicosa-11,14-dien-2-ynoate. (cis,cis isomer)

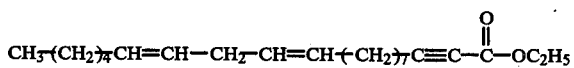

10 g (16.4 mmole) of ethyl 2-(triphenyl phosphoranylidene) 3-oxo-eicosa-11,14-dienoate is placed in a Kugelrohr apparatus. The charge is heated and the crude product of this example collected at 245°/0.3 nm. The recovered distillate is cooled, washed with petroleum ether, then filtered, and the filtrate evaporated under vacuum, to obtain crude title product of this example, which is then refined by dissolving in methylene chloride, and filtering through silica gel.

Step c) Eicosa-11,14-dien-2-ynoic acid (cis,cis isomer).

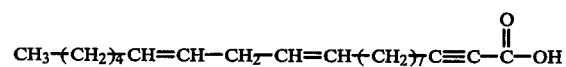

To a solution of 0.7 g (17.5 mmole) of sodium hydroxide in 50 to 75 ml of 90% ethanol (aq.) is added 5 g (15.0 mmole) of ethyl eicosa-11,14-dien-2-ynoate (cis,cis-isomer) with stirring at room temperature and the mixture stirred for about 16 hours at room temperature. The solvent is then removed on a rotary-evaporator to obtain an oily residue which is dissolved in water, the pH adjusted to from 4 to 5 by addition of 2N hydrochloric acid and the acidified mixture extracted three times with dichloroethane. The combined extracts are dried over anh. sodium sulfate, filtered and the filtrate concentrated (by evaporating under vacuum) to obtain the title product of this step as a residue, which is then refined by chromatographing on a silica gel column, eluting with chloroform.

Step d) 1-(1-oxo-eicosa-11,14-dien-2-ynyloxy)-pyrrolidine-2,5-dione (cis,cis isomer)

3.0 g (9.86 mmole) of eicosa-11,14-dien-2-ynoic acid (cis,cis-isomer) and 1.1 g (9.86 mmole) of N-hydroxysuccinimide and dissolved in 50 ml of dry glyme* under dry nitrogen gas atmosphere. 2.0 g. (0.86 mmole) of dicyclohexylcarbodiimide dissolved in 20 ml. of glyme is added dropwise with stirring, at room temperature, and the resultant mixture stirred at room temperature for a period of about 16 hours. The reaction mixture is then filtered, the filtrate concentrated (by evaporating under vacuum) to obtain a residue which is treated with pentane, the resultant mixture filtered and the filtrate concentrated (under vacuum) to obtain the title product of this example.

*glyme is dimethyl ether of ethylene glycol

Preparation 2

1-(1-Oxo-octadec-9-en-2-ynoyloxy)-pyrrolidine-2,5-dione (cis)

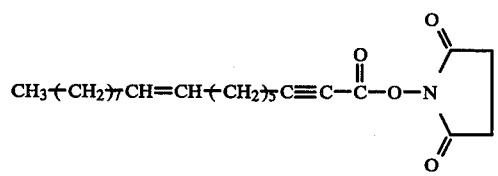

Step a) hexadec-7-enoyl chloride (cis)

$$CH_3{-}(CH_2)_7{-}CH{=}CH{-}(CH_2)_5{-}\overset{O}{\overset{\|}{C}}{-}Cl$$

To a stirred solution of 5.4 g (21.25 mmoles) of hexadec-7-enoic acid (cis) in 50 ml. of diethyl ether, is added dropwise, 18.5 ml of oxalyl chloride (98%). The resulting mixture is stirred for 2 to 4 hours at room temperature. The mixture is then concentrated by removing solvent using a rotary evaporator to obtain a residue. The residue is dissolved in methylene chloride and again concentrated using a rotary evaporator to obtain the title product of this step.

Step b)

Following the procedure of Steps a) to d) of Preparation 1, starting with the hexadec-7-enoyl chloride (cis) obtained by Step a) above, in place of the linoleoyl chloride used in Preparation 1, (and adjusting for differences in molecular weights) there is accordingly obtained 1-(1-oxo-octadec-9-en-2-ynyloxy)-pyrrolidine-2,5-dione (cis).

Repeating the procedure of this example, but using in place of the hexadec-7-enoic acid, used in step a) of this example, approximately equivalent amounts of a) octadec-7-cis enoic acid and b) oleic acid and adapting the amounts of reactants and reagents used therein, there is accordingly obtained a) 1-(1-oxo-eicos-9-cis-en-2-ynyloxy)-pyrrolidine-2,5-dione and b) 1-(1-oxo-eicos-11-cis-en-2-ynyloxy)-pyrrolidine-2,5-dione Preparation 3

1-(1-oxo-hept-2-ynyloxy)-pyrrolidine-2,5-dione

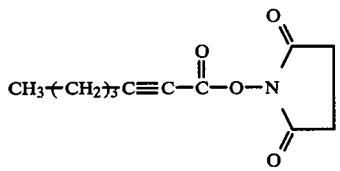

Step a hept-2-ynoic Acid

Under essentially anhydrous conditions, to a stirred solution of 3 moles of ethyl magnesium bromide in 100 ml of dry tetrahydrofuran, is added, dropwise, 25 g (3.0 mole) of 1-hexyne in 250 ml of dry tetrahydrofuran. After addition is completed the mixture is refluxed for 1½ hrs., then cooled. CO₂ (gas) is then bubbled through the mixture over a period of 4 hours. The mixture is then stirred at room temperature for about 16 hours. The reaction mixture is then poured into about 1.2 liters of ammonium chloride/ice water and stirred for about 10 minutes. The mixture is then transferred to a separatory funnel, and the pH of the mixture adjusted to 5 to 7 by addition of 2N hydrochloric acid. The mixture is then extracted 3 times with diethyl ether, dried over anh. sodium sulfate, filtered, and the filtrate concentrated under vacuum to obtain an oily residue, which is then vacuum distilled. Cuts of product distilling at 69.5°–71° at 0.3 mm (Hg) and 71.5°–72.5° at 0.3 mm are combined to obtain the title product of this step.

Step b) 1-(1-oxo-hept-2-ynyloxy)-pyrrolidine-2,5-dione

Following the procedure of Step d) of Preparation 1, but using in place of the eicosa-11,14-dien-2-ynoic acid (cis,cis) used therein, an approximately equivalent amount of hept-2-ynoic acid, there is accordingly obtained the title product of this example.

Preparation 4

1-(1-oxo-2-octyl-cyclopropandec-2-ynyloxy)pyrrolidine-2,5-dione(cis)

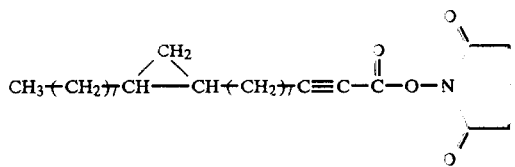

Repeating the procedure of preparation 2, but using in place of the hexadec-7-enoic acid used therein as starting material, an approximately equivalent amount of cis-2-octyl-cyclopropanoctanoic acid* there is accordingly obtained the title product.

*also called dihydrosterculic acid

Preparation 5

Repeating the procedure of Step a) of Preparation 3, but using in place of the 1-hexyne used therein, an approximately equivalent amount of a) 1-tridecyne;
b) 1-heptyne; or
c) 1-heptadecyne;

there is accordingly obtained, respectively:

a) tetradec-2-ynoic acid;
b) oct-2-ynoic acid; and
c) octadec-2-ynoic acid.

Repeating the procedure of Step d) of Preparation 1, but using in place of the eicosa-11,14-dien-2-ynoic acid (cis,cis) used therein, an approximately equivalent amount of each of the above named alkynoic acids, there is accordingly obtained:

a)  1-(1-oxo-tetradec-2-ynyloxy)-pyrrolidine-2,5-dione;
b) 1-(1-oxo-oct-2-ynyloxy)-pyrrolidine-2,5-dione; and
c)  1-(1-oxo-octadec-2-ynyloxy)-pyrrolidine-2,5-dione.

EXAMPLES OF FINAL PRODUCTS

EXAMPLE 1

Ethyl ester of N-(1-oxo-eicosa-11,14-dien-2-ynyl) tryptophan (cis, cis isomer)*

*may also be called N-[1-carbethoxy-2-(3-indolyl)ethyl]-N-(1-oxo-eicosa-11,14-cis,cis-dien-2-ynyl)amine

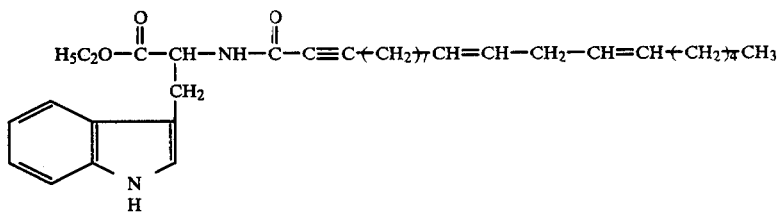

To a solution of 2.0 g (4.98 mmole) of 1-(1-oxo-eicosa-11,14-cis,cis-dien-2-ynyloxy)-pyrrolidine-2,5-dione in 50 ml CH₂Cl₂ is added 1.5 g (5.55 mmole) of d,l-tryptophan ethyl ester hydrochloride and 0.6 g triethylamine and the reaction mixture refluxed for 3 to 4 hours, then stirred at room temperature for about 16 hours. The reaction mixture is then washed with 2N hydrochloric acid, then 2N aq. sodium carbonate solution, and then brine, dried over anhydrous sodium sulfate, filtered and the filtrate evaporated (under vacuum) to obtain the crude title products as an oily residue. The residue is dissolved in chloroform and filtered through a silica gel column to obtain the refined title product as an oil.

Repeating the procedure of this example, but using in place of the d,l-tryptophan ethyl ester, used in this example, an approximately equivalent amount of d-(+)-α-methylbenzylamine there is accordingly obtained N-(1-oxo-eicosa-11,14-cis,cis-dien-2-ynyl)-d-(+)-α-methyl-benzylamine (as an oil).

EXAMPLE 2

N-[1-phenyl-2-(p-methyl-phenyl)-ethyl]-oct-2-ynoylamide*

*may also be called N-[1-phenyl-2-(p-methyl-phenyl)-ethyl]-2-octynamide or N-(1-oxo-oct-2-ynyl)-N-[α-phenyl-β-(p-methylphenyl)]ethyl amine.

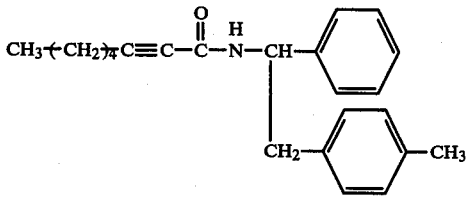

following the procedure of Example 1, but replacing the 1-(1-oxo-eicosa-11,14-cis,cis,-dien-2-ynyloxy)-pyrrolidine-2,5-dione used therein with an approximately equivalent amount of 1-(1-oxo-oct-2-ynyloxy)-pyrrolidine-2,5-dione, and replacing the d,l tryptophan ethyl ester, hydrochloride used therein with an approximately equivalent amount of α-(phenyl)-β-(p-methyl-phenyl)ethylamine, and omitting the triethylamine, there is accordingly obtained the title product, m.p. 90°–95°.

Repeating the procedure of this example, but using in place of the 1-(1-oxo-oct-2-ynyloxy)-pyrrolidine-2,5-dione used in this example, an approximately equivalent amount of a) 1-(1-oxo-octadec-7-cis-en-2-ynyl) pyrrolidine-2,5-dione or b) 1-(1-oxo-octadec-9-cis-en-2-ynyl) pyrrolidine—there is accordingly obtained respectively, a) N-[1-phenyl-2-(p-methyl-phenyl)-ethyl]-octadec-7-cis-en-2-ynoylamide, and b) N-[1-phenyl-2-(p-methyl-phenyl)-ethyl]-octadec-9-cis-en-2-ynoylamide, as a waxy solid, m.p. 53°–54°.

EXAMPLE 3

N-(1-oxo-oct-2-ynyl) tryptophan, ethyl ester

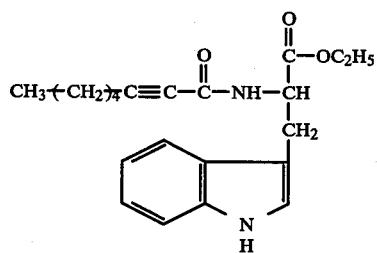

To a solution of 7.3 g (27.4 mmole) of d,l-tryptophan, ethyl ester hydrochloride, 2.7 g (27.4 mmole) of triethylamine and 75 ml of methylene chloride, in a vessel, is slowly added, with stirring, a solution of 6.5 g (27.4 mmole) of 1-(1-oxo-oct-2-ynyloxy)-pyrrolidine-2,5-dione in 75 ml of methylene chloride. When addition is complete, the mixture is refluxed for 2 to 3 hours, and then stirred at room temperature for 16 hours. The mixture is then transferred to a separatory funnel where it is washed first twice with 2N hydrochloric acid, then twice with 2N aq. sodium hydroxide, then with brine; dried over anh. sodium sulfate, filtered and the filtrate concentrated to a residue by evaporating under vacuum. The residue is refined by being taken up in chloroform and passed through a silica gel column, and concentrating the eluate (under vacuum) to a residue, which upon recrystallization from diethyl ether yields refined title product, m.p. 106°–7°.

EXAMPLE 4

N-(1-oxo-tetradec-2-ynyl),tryptophan, ethyl ester

To a vessel containing 3.6 g (13.4 mmole) of dl-tryptophan, ethyl ester hydrochloride, 1.4 g (13.4 mmole) of triethylamine dissolved in 50 ml of dichloroethane, there is slowly added at room temperature, a solution of 4.3 (13.4 mmole) of 1-(1-oxo-tetradec-2-ynyloxy)-pyrrolidine-2,5-dione in 50 ml of dichloroethane. The mixture is filtered, then refluxed for 2 hours. The reaction mixture is then cooled, and the title product recovered as described in Example 3, m.p. 67° to 70.5° (solids triturated with petroleum ether).

Repeating the procedure of this Example, but using in place of the 1-(1-oxo-tetradec-2-ynyloxy)-pyrrolidine-2,5-dione, an approximately equivalent amount of 1-(1-oxo-octadec-2-ynyloxy)-pyrrolidine-2,5-dione, there is accordingly obtained N-(1-oxo-octadec-2-ynyl)-tryptophan, ethyl ester, m.p. 67°–68.5°.

EXAMPLE 5

N-[d-(+)-α-methylbenzyl]-oct-2-ynoylamide

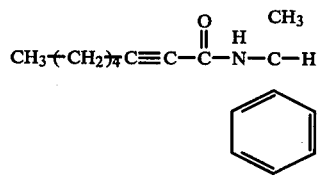

Repeating the procedure of Example 1, but using in place of the dl, tryptophan, ethyl ester hydrochloride used therein, an approximately equivalent amount of d-(+)-α-methylbenzylamine and omitting the triethylamine, there is accordingly obtained the title product (as an oil).

Repeating the procedure of this example, but using in place of the 1-(1-oxo-oct-2-ynyloxy)-pyrrolidine-2,5-dione, an approximately equivalent amount of a) 1-(1-oxo-tetradec-2-ynyloxy-pyrrolidine-2,5-dione;
b) 1-(1-oxo-octadec-2-ynyloxy)-pyrrolidine-2,5-dione;
c) 1-(1-oxo-eicos-7-cis-en-2-ynyloxy)-pyrrolidine-2,5-dione;
d) 1-(1-oxo-octyl-cyclopropano-dec-2-ynyloxy)-pyrrolidine-2,5-dione; or
e) 1-(1-oxo-eicos-11-cis-en-2-ynyloxy)-pyrrolidine-2,5-dione;

there is accordingly obtained:
the secondary d-(+)-α-methylbenzyl amides of:
a) tetradec-2-ynoic acid (as an oil);
b) octadec-2-ynoic acid (m.p. 66°–68°);
c) eicos-7-cis-en-2-ynoic acid;
d) cis-octyl-cyclopropanodec-2-ynoic acid; and
e) eicos-11-cis-en-2-ynoic acid (as an oil).

EXAMPLE 6

N-[α-(p-methylbenzyl)-β-(p-methylphenyl)ethyl]-oct-2-ynoylamide.

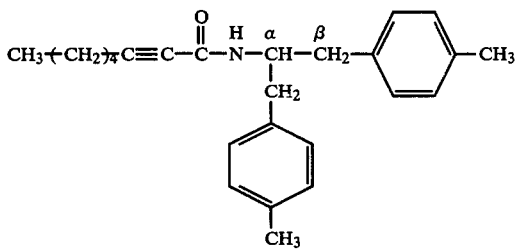

Repeating the procedure of example 2, but using in place of the α-phenyl-β-(p-methylphenyl)-ethylamine used therein, an approximately equivalent amount of α-(p-methylbenzyl)-β-(p-methylphenyl)ethylamine there is accordingly obtained the title product, m.p. 90°–94°.

Repeating the procedure of this example, but using in place of the 1-(1-oxo-oct-2-ynyloxy)-pyrrolidine-2,5-dione used in this example, an approximately equivalent amount of a) 1-(1-oxo-octadec-2-ynyloxy)-pyrrolidine-2,5-dione or b) 1-(1-oxo-octadeca-9-cis-en-2-ynyloxy-pyrroline-2,5 dione there is accordingly obtained a) N-[α-(p-methylbenzyl)-β-(p-methylphenyl)ethyl]-octadec-2-ynoylamide, m.p. 58°–60°, and b) N-[α-p-methylbenzyl)-β-(p-methylphenyl)ethyl]-octadeca-9-cis-en-2-ynoylamide, as an oil.

EXAMPLE 7

N-[1-phenyl-2-(4-methylphenyl)]ethyl, octadec-2-ynoylamide

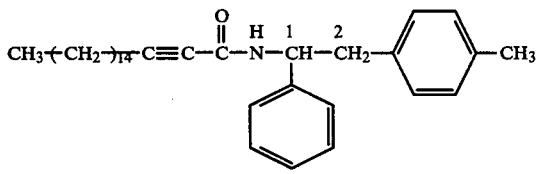

Step a  1-(1-oxo-octadec-2-ynyloxy)-pyrrolidine-2,5-dione.

3.0 g (0.011 mole) of octadec-2-ynoic acid and 1.8 (0.011 mole) of 1-hydroxy-pyrrolidine-2,5-dione are dissolved in about 150 ml glyme in a vessel and 2.2 g of DCC in about 100 dl of glyme is added thereto, dropwise. A precipitate forms and the mixture is stirred at room temperature for about 16 hours to obtain a reaction mixture containing the title product of this step (as a precipitate).

Step B N-[1-phenyl-2-(4-methylphenyl)]ethyl, octadec-2-ynoylamide

The mixture resulting from Step a) above, is filtered to recover solids washed with glyme, then dissolved in 250 ml methylenechloride and placed in a vessel. 3.8 g (0.018 mole) of 1-(phenyl)-2-(p-methylphenyl)ethylamine is added thereto, dropwise. After the addition is completed the mixture is refluxed for 2 hours, then stirred at room temperature for about 18 hours to obtain a reaction mixture (containing the title product of this step).

The resultant reaction mixture is washed twice with 2N hydrochloric acid, then twice with 2N aqueous sodium hydroxide solution, then with brine. The organic phase is dried over anh. sodium sulfate, then concentrated (by removing solvent under vacuum) to obtain a residue. The residue is taken up in diethylether and recrystallized twice to yield refined title product, m.p. 85°–90°.

EXAMPLE 8

Ethyl ester of N-(1-oxo-eicos-11-cis-en-2-ynyl) tryptophan

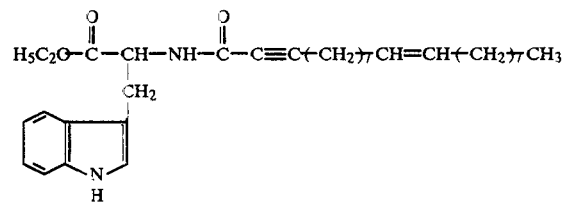

Repeating the procedure of Example 1, but using in place of the 1-(1-oxo-eicosa-11,14-cis,cis-dien-2-ynyloxy)-pyrrolidine-2,5-dione used therein, an approximately equivalent amount of 1-(1-oxo-eicos-11-cis-en-2-ynyloxy pyrrolidine-2,5-dione, there is accordingly obtained the title product of this example as a low melting wax.

EXAMPLE 9

N-[α-(benzyl)-β-(phenyl)ethyl]-oct-2-ynoylamide

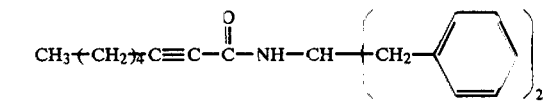

Repeating the procedure of example 2, but using in place of the α-(phenyl)-β-(p-methylphenyl)ethylamine, used therein, an approximately equivalent amount of α-(benzyl)-β-(phenyl)ethylamine there is accordingly obtained the title product of this example, m.p. 90°–95° C.

Repeating the procedure of this example, but using in place of the 1-(1-oxo-oct-2-ynyloxy)-pyrrolidine-2,5-dione used in this example, an approximately equivalent amount of a) 1-(1-oxo-eicosa-11,14-cis,cis-dien-2-ynyloxy)-pyrrolidine-2,5-dione;

b) 1-(1-oxo-octadec-2-ynyloxy)-pyrrolidine, 2,5-dione;

c) 1-(1-oxo-eicosa-7-cis-en-2-ynyloxy)-pyrrolidine-2,5-dione;

d) 1-(1-oxo-octyl-cyclopropano-dec-2-ynyloxy)-pyrrolidine-2,5-dione; or e) 1-(1-oxo-octadeca-9-cis-en-2-ynyloxy)-pyrrolidine-2,5-dione;

there is accordingly obtained:

a) N-[α-(benzyl)-β-(phenyl)ethyl]eicosa-11,14-cis,cis-dien-2-ynoylamide;

b) N-[α-(benzyl)-β-(phenyl)ethyl]octadec-2-ynoylamide;

c) N-[α-(benzyl)-β-(phenyl)ethyl]eicos-7-cis,-en-2-ynoylamide, d) N-[α-(benzyl)-β-(phenyl)ethyl]octyl-cyclopropano-dec-2-ynoylamide; and e) N-[α-(benzyl)-β-(phenyl)ethyl]-octadeca-9-cis-en-2-ynoylamide, as an oil.

EXAMPLE 10

Repeating the procedure of example 2, but using in place of the 1-(1-oxo-oct-2-ynyloxy)-pyrrolidine-2,5-dione used therein, an approximately equivalent amount of a) 1-(1-oxo-but-2-ynyloxy)-pyrrolidine-2,5-dione or b) 1-(1-oxo-hex-2-ynyloxy)-pyrrolidine-2,5-dione; there is accordingly obtained: a) N-[1-phenyl-2-(p-methyl-phenyl)ethyl]-but-2-ynoylamide, m.p. 115°–120°, and b) N-[1-phenyl-2-(p-methyl-phenyl)-ethyl]-hex-2-ynoylamide, m.p. 105°–110°.

What is claimed is:

1. A compound of the formula:

$$A-C\equiv C-\overset{O}{\underset{\parallel}{C}}-NH-B$$

wherein A is of type a) an alkyl radical having from 1 to 23 carbon atoms;

type b) an alkenyl or alk-(poly)en-yl radical having from 7 to 23 carbon atoms and from 1 to 4 ethylenically unsaturated positions; or type c) a saturated hydrocarbon chain having from 7 to 23 carbon atoms and 1 to 4 cyclopropanyl groups of the formula $$-CH\underset{\underset{CH-}{\diagdown}}{\overset{\diagup CH_2}{}}$$

and B is of:

type a) an aralkyl radical of the structure

[structure with $-CH(R^3)-(CH_2)_g-$ phenyl with $R^1, R^2$]

wherein g is 0 or 1;
wherein
  $R^1$ is a hydrogen atom, halo having an atomic weight of from about 19 to 80, alkoxy having from 1 to 3 carbon atoms; or alkyl having from 1 to 3 carbon atoms;
  $R^2$ is a hydrogen atom, alkyl having from 1 to 3 carbon atoms, alkoxy having from 1 to 3 carbon atoms, or halo having an atomic weight of from about 19 to 36; and
  $R^3$ is i) a hydrogen atom, a phenyl radical of the structure ii)

(ii) [phenyl ring with y, y']

wherein
  y is a hydrogen atom, halo having an atomic weight of from about 19 to 80, alkoxy having from 1 to 3 carbon atoms, or alkyl having from 1 to 3 carbon atoms; and
  y' is a hydrogen atom, alkoxy having from 1 to 3 carbon atoms, alkyl having from 1 to 3 carbon atoms, or halo having an atomic weight of from about 19 to 36; or of subtype iii, a benzyl radical of the formula (iii) [−CH₂− phenyl ring with y, y']

wherein
  y and y' are as defined above; or subtype iv) alkyl having from 1 to 8 carbon atoms;

type b) a phenyl radical of the structure of:

[phenyl ring with R°, R²]

wherein
  $R^2$ is as defined above, and
  $R°$ is a hydrogen atom, halo having an atomic weight of from about 19 to 80, alkyl having from 1 to 3 carbon atoms; alkoxy having from 1 to 3 carbon atoms; or a radical of the structure R/:

[−(D)$_f$− phenyl ring with Q]

in which
  D is —CH₂— or —O—;
  f is 0 or 1; and
  Q is a hydrogen atom, halo having an atomic weight of from about 19 to 80, alkoxy having from 1 to 3 carbon atoms, or alkyl having from 1 to 3 carbon atoms;

or type c) a benzocycloalkyl nucleus of the structure:

[bicyclic structure with (CH₂)$_j$, R¹, R²]

wherein
  $R^1$ and $R^2$ are as defined above; and
  j is a whole integer of from 1 to 4.

2. A compound of claim 1 in which B is a type a).
3. A compound of claim 1 in which B is of type b).
4. A compound of claim 1 in which B is of type c).
5. A compound of claim 1 in which A is of type a).
6. The compound of claim 5 in which is N-[1-phenyl-2-(p-methyl-phenyl)ethyl]-oct-2-ynoylamide.
7. The compound of claim 5 which is N-[α-(p-methyl-benzyl)-β-(p-methylphenyl)-ethyl]-oct-2-ynoylamide.
8. The compound of claim 5 which is N-[d-(+)-α-methylbenzyl]oct-2-ynoylamide.
9. The compound of claim 5 which is N-[d-(+)-α-methylbenzyl]-tetradec-2-ynoylamide.

10. The compound of claim 5 which is N-[d-(+)-α-methylbenzyl]-octadec-2-ynoylamide.

11. The compound of claim 5 which is N-[1-phenyl-2-(4-methylphenyl)-ethyl]-octadec-2-ynoylamide.

12. The compound of claim 5 which is N-[α-(p-methylbenzyl)-β-(p-methylphenyl)ethyl]-octadec-2-ynoylamide.

13. The compound of claim 5 which is N-(1-phenyl-2-(p-methyl-phenyl)-ethyl]-but-2-ynoylamide.

14. The compound of claim 5 which is N-[1-phenyl-2-(p-methyl-phenyl)-ethyl]-hex-2-ynoylamide.

15. The compound of claim 5 which is N-[α-(benzyl)-β-(phenyl)ethyl]-oct-2-ynoylamide.

16. A compound of claim 1 in which A is of type b).

17. The compound of claim 16 which is N-(1-eicosa-11,14-cis,cis-dien-2-ynyl)-d-(+)-α-methylbenzylamine.

18. The compound of claim 16 which is N-[α-methylbenzyl]eicos-11-cis-en-2-ynoylamide.

19. The compound of claim 16 which is N-[1-phenyl-2-(p-methyl-phenyl)-ethyl]octadec-9-cis-en-2-ynoylamide.

20. The compound of claim 16 which is N-[α-p-methylbenzyl)-β-(p-methylphenyl)ethyl]-octadeca-9-cis-en-2-ynoylamide.

21. The compound of claim 16 which is N-[α-(benzyl)-β-(phenyl)ethyl]-octadeca-9-cis-en-2-ynoylamide.

22. A pharmaceutical composition suitable for inhibiting the accumulation of cholesterol ester in the arterial wall of a mammal comprising an amount of a compound of claim 1 effective in inhibiting the accumulation of cholesterol ester and a non-toxic pharmaceutically-acceptable carrier.

23. A composition of claim 22 in which the compound is present in an amount of from about 13 milligrams to about 2,500 milligrams.

24. A composition of claim 22 in a solid form.

25. A composition of claim 22 in which the carrier is solid.

26. A composition of claim 22 in which the carrier is liquid.

27. A composition of claim 22 in which the compound is N-[1-phenyl-2-(p-methylphenyl)-ethyl]oct-2-ynoylamide.

28. A method of inhibiting the accumulation of cholesterol ester in the arterial wall of a mammal in need of such treatment, comprising administering an amount of a compound of claim 1 to said mammal effective in inhibiting the accumulation of cholesterol ester in the arterial walls of said mammal.

29. A method of claim 28 in which the compound is administered in an amount of from about 100 milligrams to about 5,000 milligrams per day.

30. A method of claim 28 in which the compound is administered in an amount of from about 100 milligrams to about 2,000 milligrams per day.

31. A method of claim 28 in which the compound is N-[1-phenyl-α-(p-methylphenyl)-ethyl]oct-2-ynoylamide.

* * * * *